United States Patent [19]

Hongo

[11] Patent Number: 4,501,277
[45] Date of Patent: Feb. 26, 1985

[54] SELECTED BEAM MARKING SYSTEM FOR RAPID ULTRASOUND MEASUREMENTS

[75] Inventor: Hironobu Hongo, Ootawara, Japan

[73] Assignee: Tokyo Shibaura Denki Kabushiki Kaisha, Kawasaki, Japan

[21] Appl. No.: 426,133

[22] Filed: Sep. 28, 1982

[30] Foreign Application Priority Data

Nov. 12, 1981 [JP] Japan ................. 56-180382

[51] Int. Cl.³ ............................................. A61B 10/00
[52] U.S. Cl. ..................................... 128/660; 128/663
[58] Field of Search ................................. 128/660–663; 73/861.25

[56] References Cited

U.S. PATENT DOCUMENTS

| 4,141,347 | 2/1979 | Green | 128/663 |
| 4,217,909 | 8/1980 | Papadofrangakis | 128/663 |
| 4,318,413 | 3/1982 | Iinuma | 128/663 |
| 4,346,717 | 8/1982 | Haerten | 128/660 |
| 4,398,540 | 8/1983 | Takemura | 128/661 |
| 4,413,630 | 11/1983 | Anderson | 128/661 |
| 4,416,286 | 11/1983 | Iinuma | 128/663 |

FOREIGN PATENT DOCUMENTS 490105 12/1974 Australia .
10304 4/1980 European Pat. Off. ............ 128/663
1404783 9/1975 Fed. Rep. of Germany .

Primary Examiner—Kyle L. Howell
Assistant Examiner—Francis J. Jaworski
Attorney, Agent, or Firm—Cushman, Darby & Cushman

[57] ABSTRACT

An ultrasonic pulse Doppler apparatus comprising an ultrasonic probe for transmitting ultrasonic beam into an object and receives the echoes from the object, a first processing circuit for processing the echoes received by the probe to form data of a B scan tomogram, a first monitor for displaying the B scan tomogram, beam mark setting circuit for setting a plurality of beam marks on the B scan tomogram, measuring point setting circuit for setting a plurality of blood flow measuring points on each of the beam marks, beam mark selecting circuit for selecting any one of the plurality of beam marks, measuring point selecting circuit for selecting any one of the plurality of blood flow measuring points on the selected beam mark, a second processing circuit for processing the echoes received by said probe to form a signal of a blood flow velocity at the selected measuring point, a second monitor for displaying the blood flow velocity at the selected measuring point, and modulating circuit for distinguishing the selected measuring point on the selected beam mark from other measuring points.

8 Claims, 10 Drawing Figures

SELECTED BEAM MARKING SYSTEM FOR RAPID ULTRASOUND MEASUREMENTS

BACKGROUND OF THE INVENTION

The present invention relates to an ultrasonic pulse Doppler apparatus capable of displaying a tomogram on a specific part of an object under diagnosis, a plurality of ultrasonic beam marks, a plurality of blood flow measuring points, and a blood flow velocity signal at a specific measuring point selected from the plurality of measuring points on different monitor screens.

In a prior art ultrasonic pulse Doppler apparatus, a tomogram on a specific part of an object under diagnosis and a blood flow velocity signal at a specific point or a specific blood flow measuring point are displayed as shown in FIG. 1, for example. As shown, a monitor screen 1 displays a B mode tomogram formed by scanning the object in a sectorial fashion and a blood flow measuring point set on a beam mark 3. Another monitor screen 4 displays an M mode image 5 representing a variation of a tissue along a beam mark 3 with time and a blood flow velocity signal 6 at the measuring point.

The Doppler frequency shift $f_d$ is expressed by an equation $f_d = 2Vf_o \cos\theta/C$ where $f_o$ is a frequency of a transmitted ultrasonic wave, V a blood flow velocity, C a velocity of the ultrasonic wave propagating in an object under diagnosis, and $\theta$ an angle of the ultrasonic beam with respect to a direction of blood flow. As seen from the equation describing a proportional relation between the Doppler frequency shift $f_d$ and the blood flow velocity, the blood flow can be obtained by detecting the Doppler frequency shift $f_d$.

The number of measuring points which can be set by the prior art Doppler apparatus is only one, as shown in FIG. 1. An accurate diagnosis, however, needs blood flow velocities measured quickly at a plurality of measuring points. For measuring blood flow velocities at different measuring points using the prior Doppler apparatus, the measuring point must be positioned again for each measurement of the blood flow velocity. Such positioning work of the measuring points takes a relatively long time. Thus, the prior art Doppler apparatus has not successfully satisfied such need.

SUMMARY OF THE INVENTION

Accordingly, an object of the present invention is to provide an ultrasonic pulse Doppler apparatus which may instantaneously and sequentially measure blood flow velocities at different positions by a simple operation.

According to the invention, there is provided an ultrasonic pulse Doppler apparatus comprising:
an ultrasonic probe for transmitting an ultrasonic beam into an object and receiving the echoes from said object;
a first processing means (10a, 10c) for processing the echoes received by said probe to form data of a B scan tomogram of said object;
a first display means for displaying the B scan tomogram;
beam mark setting means for setting at least one beam mark on the B scan tomogram;
measuring point setting means for setting a plurality of blood flow measuring points on said beam mark;
measuring point selecting means for selecting any one blood flow measuring point from said plurality of blood flow measuring points;
a second processing means for processing the echoes received by said probe to form a signal of a blood flow velocity at a selected measuring point;
a second display means for displaying the blood flow velocity at the selected measuring point; and
modulating means for distinguishing the selected measuring point on said beam mark from other measuring points on said beam mark.

According to the invention, there is further provided an ultrasonic pulse Doppler apparatus comprising:
an ultrasonic probe for transmitting ultrasonic beam into an object and receives the echoes from said object;
a first processing means for processing the echoes received by said probe to form data of a B mode tomogram of said object;
a first display means for displaying the B scan tomogram;
beam mark setting means (11) for setting a plurality of beam marks on the B scan tomogram;
measuring point setting means for setting a plurality of blood flow measuring points on each of said beam marks;
beam mark selecting means for selecting any one of said plurality of beam marks;
measuring point selecting means for selecting any one of said plurality of blood flow measuring point;
a second processing means for processing the echoes received by said probe to form a signal of a blood flow velocity at the selected measuring point;
a second display means for displaying the blood flow velocity at the selected measuring point; and
modulating means for distinguishing said selected measuring point on the selected beam mark from other measuring points.

DETAILED DESCRIPTION OF THE PREFERRED EMBODIMENT

Figure 1:
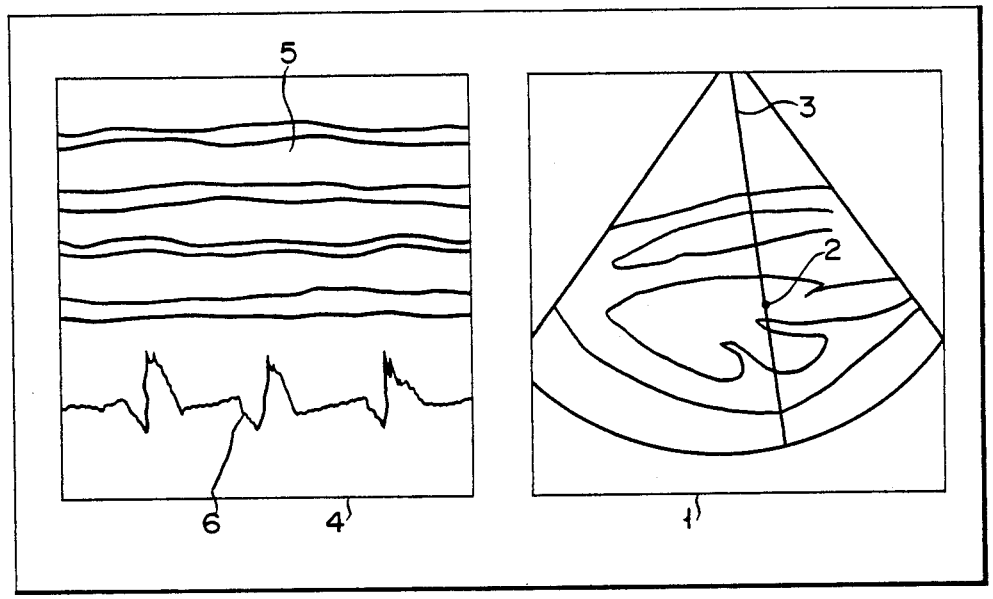
FIG. 1 illustrates display modes displayed on monitor screens of the prior ultrasonic pulse Doppler apparatus.
Figure 2:
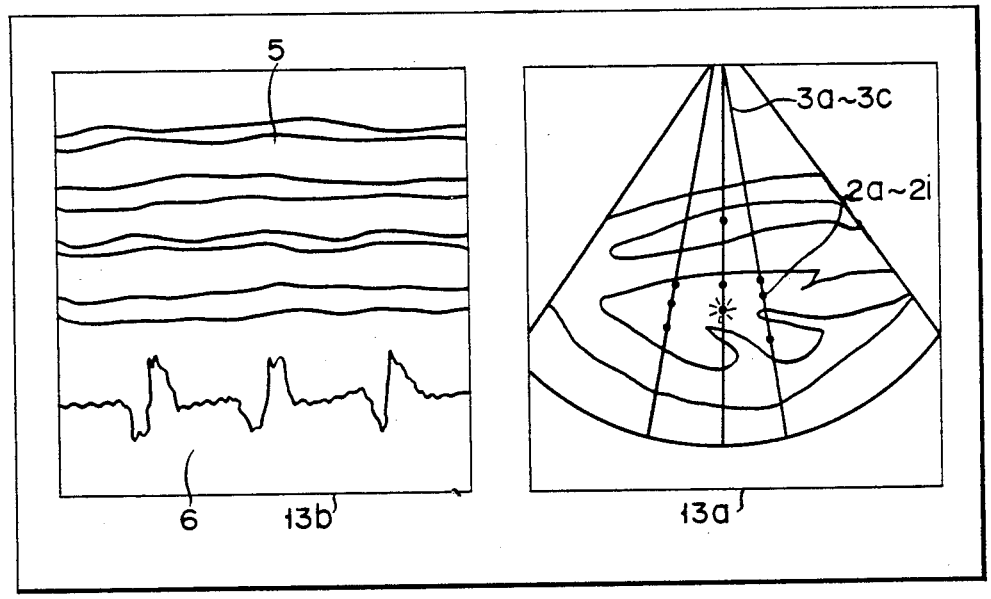
FIG. 2 illustrates display tomograms on monitor screens of a ultrasonic pulse Doppler apparatus according to the present invention.

An ultrasonic pulse Doppler apparatus according to the present invention is comprised of a signal generator 7, a scanning controller 8, a transducer controller 9, a display mode controller 10, a beam mark setting circuit 11, a measuring point setting circuit 12, two monitors 13a and 13b, and a sector scanning type ultrasonic transducer probe 14.

In the signal generator 7, a clock pulse generator 7a produces a clock pulse signal at 19.2 MHz, for example. A first frequency divider 7b frequency-divides the clock pulse signal from the generator 7a to produce a rate pulse signal at a given frequency, for example, 4 KHz. A second frequency divider 7c receives the rate pulse signal from the frequency divider 7b to produce a pulse signal to define a rate of scanning for obtaining a B mode image signal, an M mode image signal and a blood flow velocity signal. A third frequency divider 7d frequency-divides the pulse signal from the second frequency divider 7c to form a pulse signal at such a frequency, for example, several Hz, so as to allow human eyes to visually follow the setting of beam marks 3a to 3c and blood flow measuring points 2a to 2i on a B mode image. A first gate circuit 7e converts the rate pulse signal from the first frequency divider 7b to a rate pulse signal for obtaining an M mode image and a blood flow velocity signal according to the pulse signal from the second frequency divider 7b. A second gate circuit 7f converts the rate pulse signal from the first frequency divider 7b into a rate pulse signal for obtaining a B mode according to the output pulse signal from the second frequency divider 7c. For setting to 1:1 a ratio of the scanning rates of the B mode image to the M mode image signals and the blood flow velocity signal, a dividing ratio of the second frequency divider 7c is set to ½.

Figure 8:
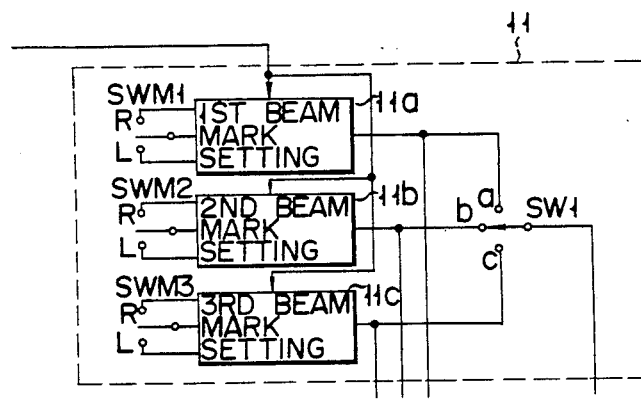
FIG. 8 is a block diagram of a beam mark setting circuit used in the Doppler apparatus shown in FIG. 3A.

The scanning controller 8 controls the scannings for forming the B mode image, the M mode image and the blood flow velocity signal. The scanning controller 8 is comprised of first to third scanning control circuits for beam marks 8a to 8c, a scanning control circuit 8d for the M mode image, another scanning control circuit 8e for the B mode image, a first adder 8f and a second adder 8g. The first to third scanning control circuits 8a to 8c encode the beam marks 3a to 3c set by setting circuits 11a to 11c in a beam mark setting circuit 11 (FIG. 8) and produce the coded signals in synchronism with the output pulse signal from the second gate circuit 7f. The scanning control circuit 8d produces one coded signal selected by a switch SW1 of the beam mark setting circuit 11, as an M mode control signal, in synchronism with an output pulse signal from the first gate circuit 7e. The scanning control circuit 8e responds to a clock pulse signal from the second gate circuit 7f to alternately produce the coded signals corresponding to the individual scanning lines for forming a B mode image and the coded signals corresponding to the individual transducer elements of a probe 14. The first adder 8f adds together the coded signals produced from the scanning control circuit 8d and 8e. The second adder 8g adds together the coded signals produced from the scanning control circuits 8a to 8c and the scanning control circuit 8e.

The transducer controller 9 drives an array of the transducer elements of the probe 14 according to the coded signals produced from the first adder 8f of the scanning controller 8 to cause the probe 14 to project an ultrasonic wave toward the object under diagnosis. The transducer controller 9 receives the echoes of the ultrasonic wave returned from the object to convert them into electrical signals. The transducer controller 9 includes a transducer scanning circuit 9a and a transmit/-receive (T/R) circuit 9b. The transducer scanning circuit 9a controls the operation of the transducer elements. The transmit/receive (T/R) circuit 9b generates a rate pulse signal according to an output signal from the scanning circuit 9a and drives the transducer elements of the probe 14 with the rate pulse signal applied, and further amplifies the signals of the echoes received by and applied from the probe 14.

The display mode controller 10 controls the display modes so that a B mode image is displayed on the monitor 13a, and an M mode image and a blood flow signal are displayed on the monitor 13b. The display mode controller 10 is comprised of a third adder 10a, a Doppler signal detecting circuit 10b, a B mode display control circuit 10, a fourth adder 10d, and an M mode image/blood flow velocity signal display control circuit 10e. The third adder 10a adds an intensity modulation signal produced from a blood flow measuring point setting circuit 12 for setting three measuring points 2a to 2c, 2d to 2f and 2g to 2on the beam marks 3a to 3c, as shown, and an echo signal produced from the T/R circuit 9b. The Doppler signal detecting circuit 10b detects a Doppler frequency shift at one selected measuring point of these points 2a to 2i, in synchronism with the M mode image scanning signal produced from the first gate circuit 7e in the signal generator 7. A B mode image display control circuit 10c receives a B mode image scanning signal from the second adder 8g in the scanning controller 8 and an intensity modulation signal from the third adder 10a to produce signals for displaying the B mode image (i.e. B scan tomogram), the beam marks, the blood flow measuring points on the monitor 13a. A fourth adder 10d adds a Doppler signal produced from the Doppler signal detecting circuit 10b and an M mode signal produced from the third adder 10. The M mode/blood flow velocity signal display control circuit receives an output signal from the first gate circuit 7e and an output signal from the fourth adder 10d to produce signals for displaying the M mode image and the blood flow velocity signal on the monitor 13b.

The beam mark setting circuit 11 determines positions of the monitor 13a. The beam mark setting circuit 11 is comprised of switches SWH1 to SWH3, first to third beam mark setting circuits 11a to 11c, and a switch SW1. The switches SWM1 to SWM3 horizontally move and desirably position the beam marks 3a to 3c on a B mode image displayed on a monitor 13a. The first to third beam mark setting circuits 11a to 11c produce signals indicating the beam marks 3a to 3c positioned by means of the switches SWM1 to SWM3, respectively. The switch SW1 selects any of these output signals from the beam mark setting circuits 11a to 11c and sends it to the scanning control circuit 8d.

Figure 3A:
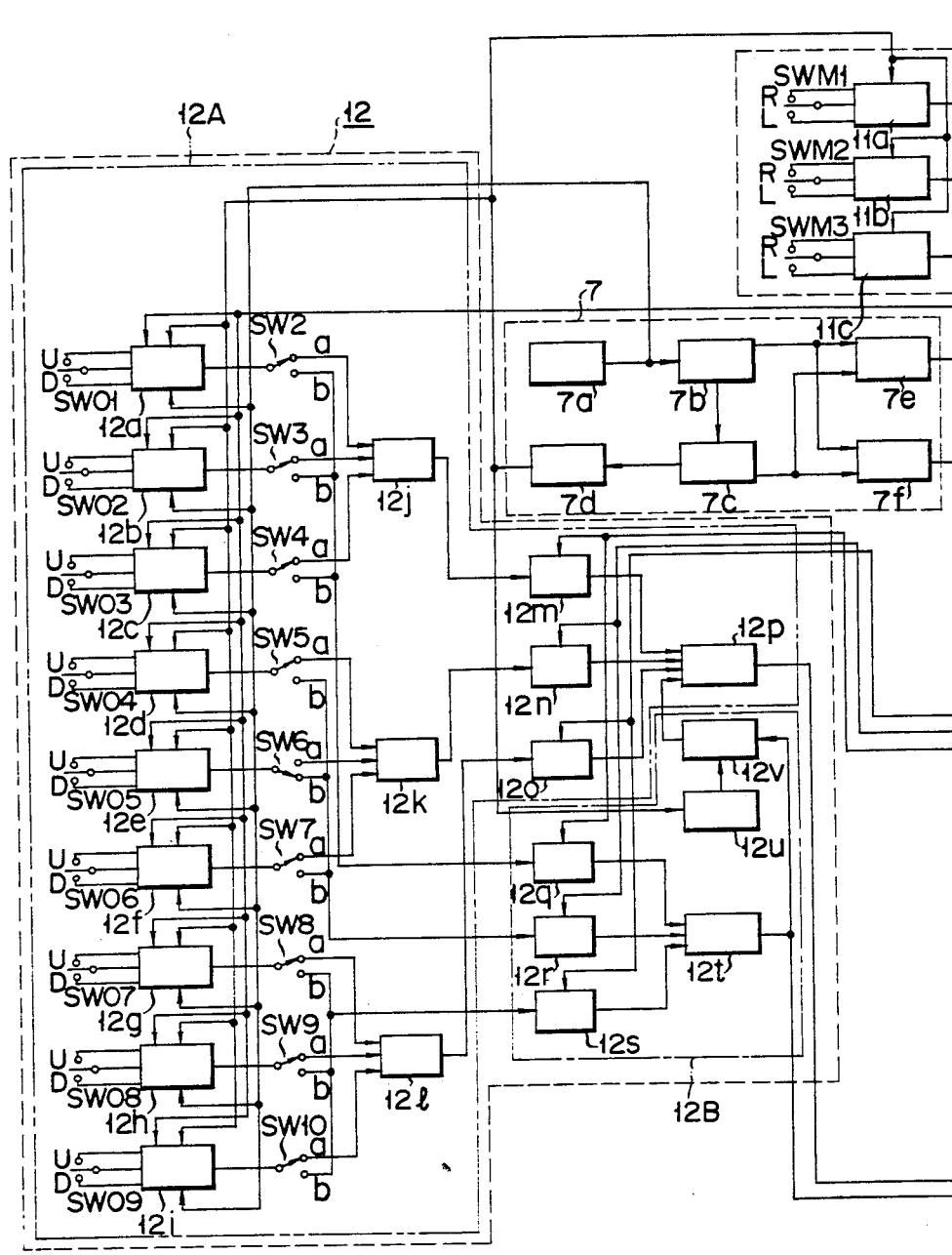
FIGS. 3A and 3B are schematic block diagrams of an arrangement of an ultrasonic pulse Doppler apparatus according to the present invention.
Figure 3B:
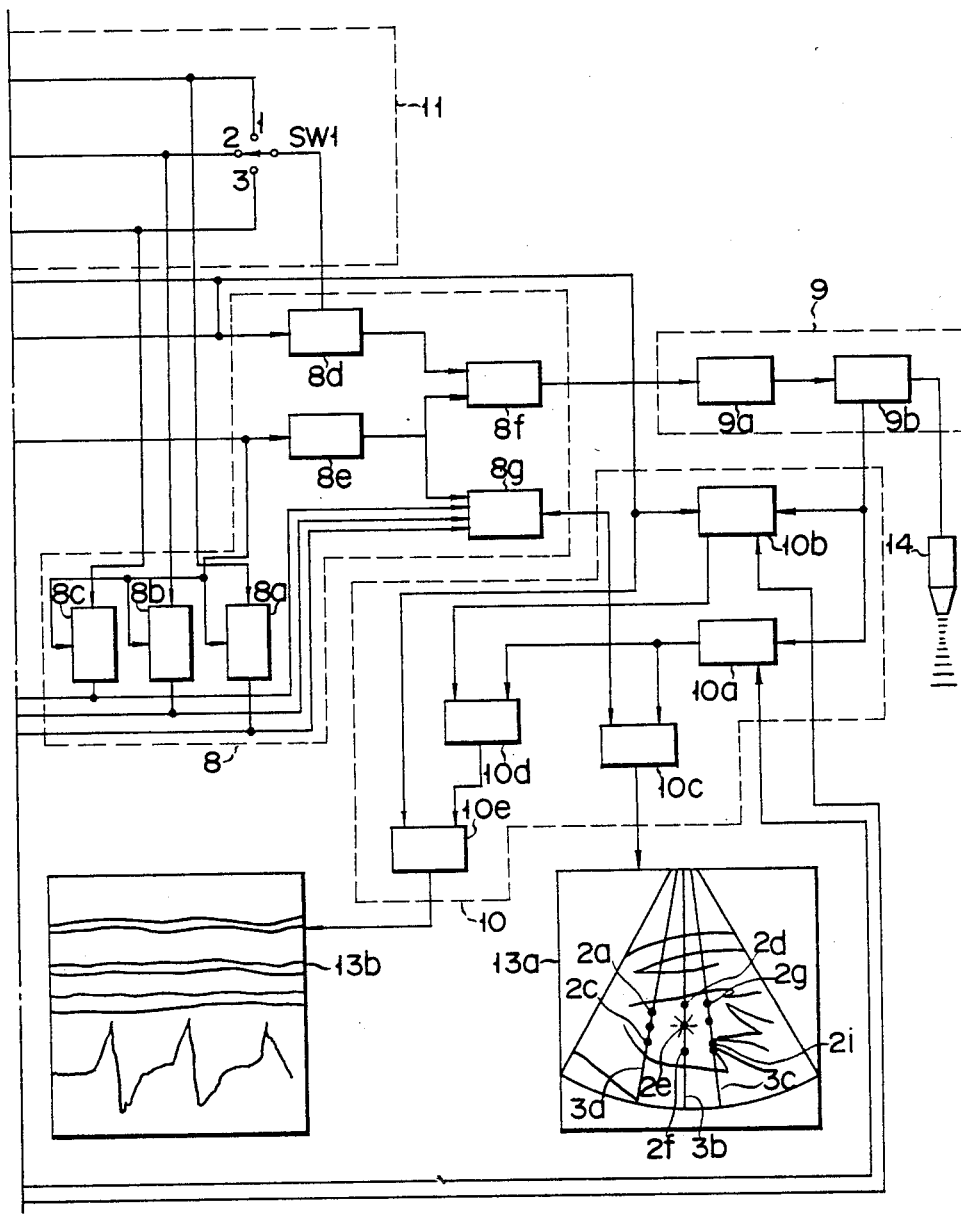
Figure 4:
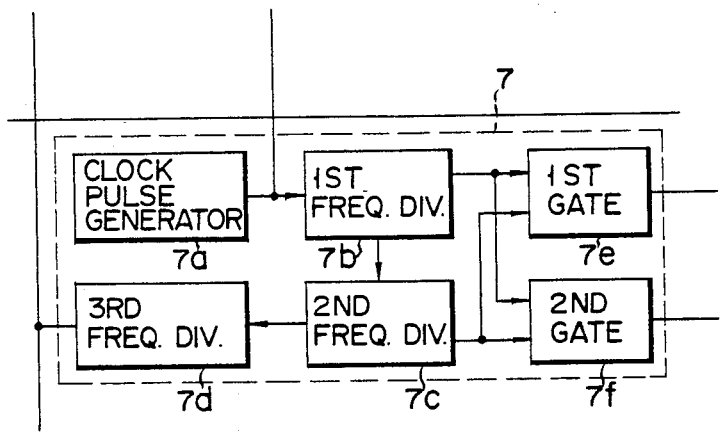
FIG. 4 is a block diagram of a signal generator used in the Doppler apparatus shown in FIG. 3A.
Figure 5:
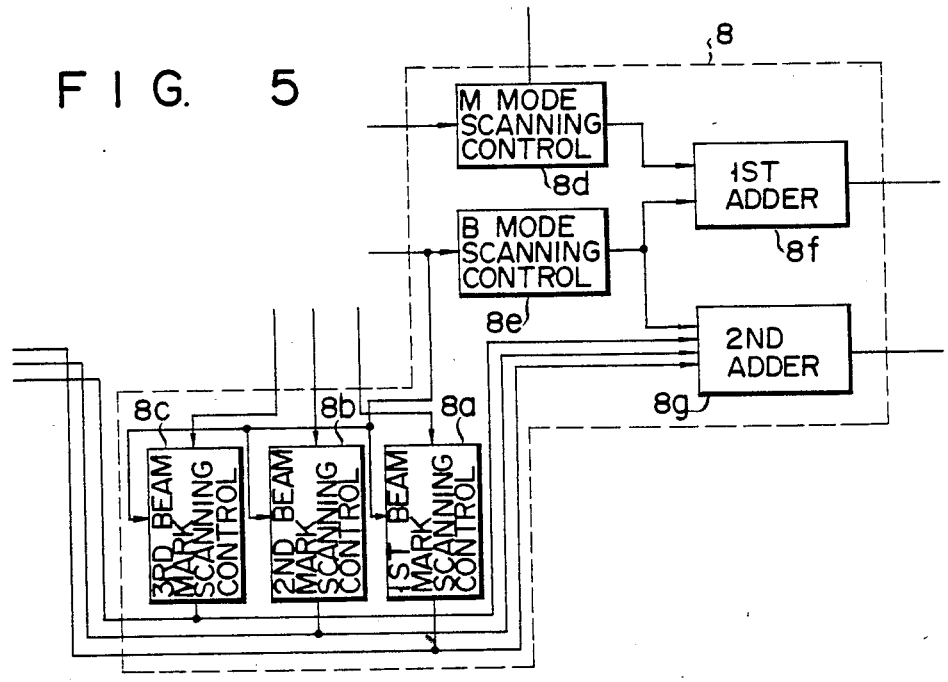
FIG. 5 is a block diagram of a scanning controller used in the Doppler apparatus shown in FIG. 3B.
Figure 6:
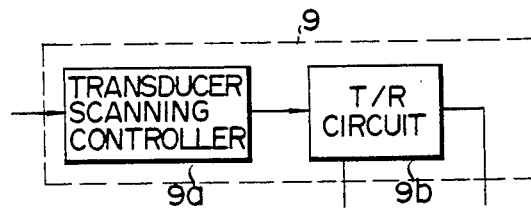
FIG. 6 is a block diagram of an ultrasonic wave transmit/receive circuit used in the Doppler apparatus shown in FIG. 3B.
Figure 7:
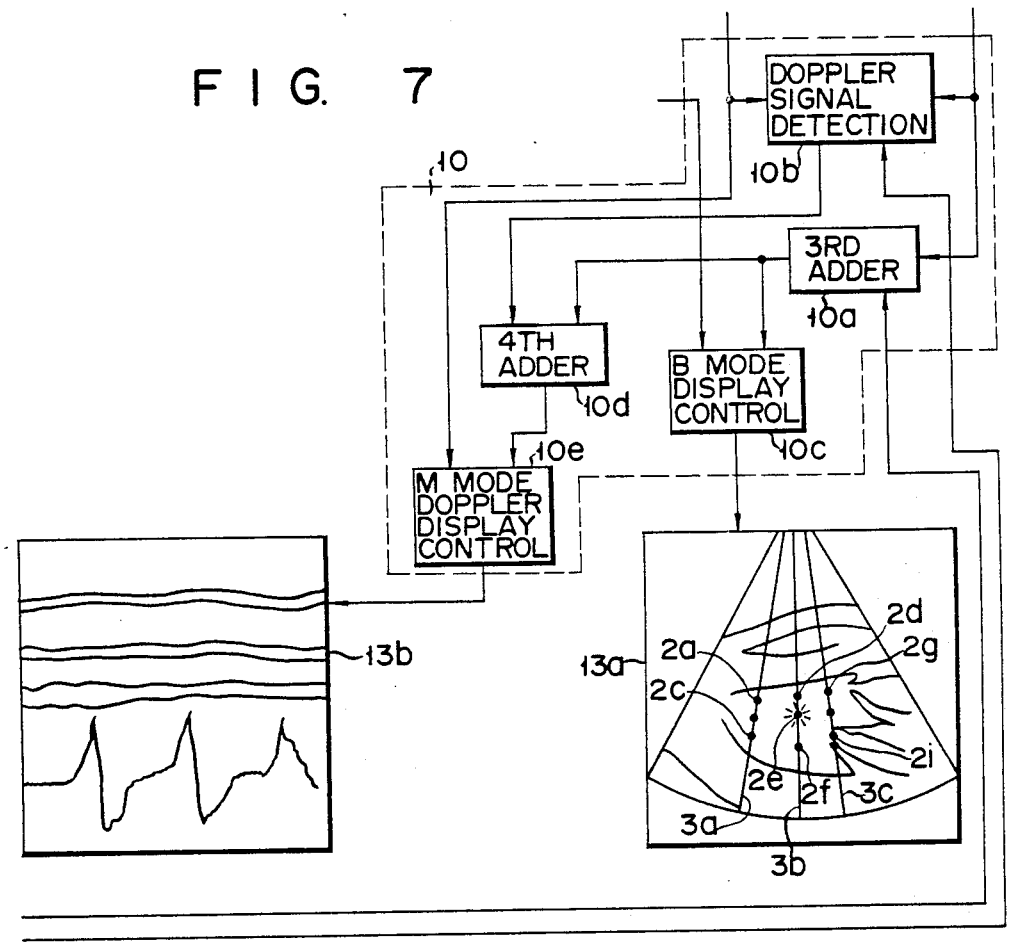
FIG. 7 is a block diagram of a display mode controller used in the Doppler apparatus shown in FIG. 3B.
Figure 9:
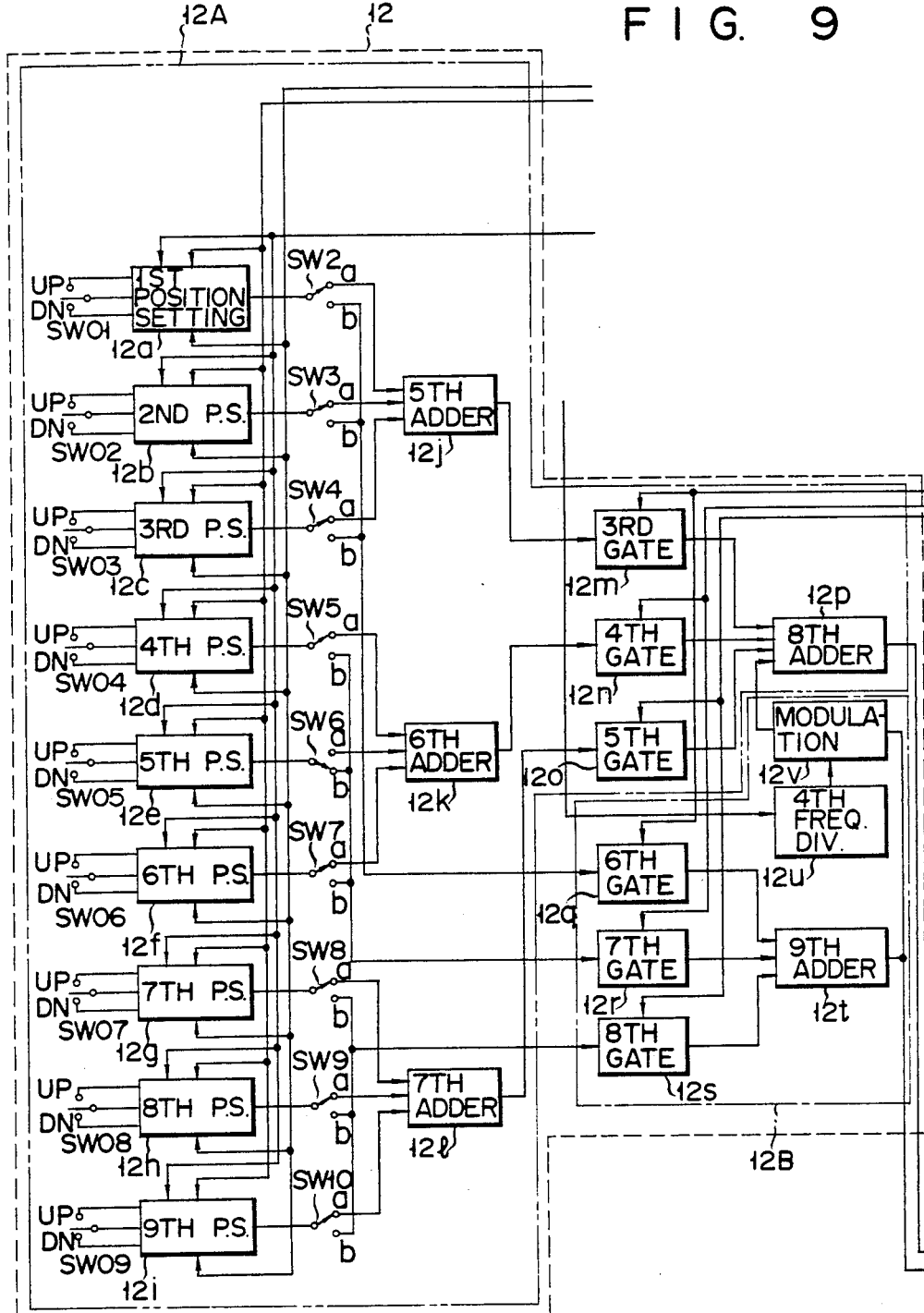
FIG. 9 is a block diagram of a measuring point setting circuit used in the Doppler circuit shown in FIG. 3A.

The blood flow measuring point setting circuit 12 is comprised of a blood flow measuring unit 12A and a blood flow measuring select unit 12B, as shown in FIG. 9. The measuring point setting unit 12A positions the blood flow measuring points 2a to 2c, 2d to 2f, and 2g to 2i on the beam marks 3a to 3c displayed on the B mode image monitor 13a. The measuring point select unit 12B selects any one of the measuring points 2a to 2i to display a blood flow velocity at the selected measuring point on the monitor 13b. The blood flow measuring points 2a to 2i are more intensively displayed and particularly the selected measuring point 2e on the monitor 13a in FIG. 3B is flickered to distinctly indicate the measuring point of which the blood flow velocity signal is now displayed on the monitor 13b.

In the measuring point setting circuit 12A, nine switches SW01 to SW09 vertically move and desirably position the measuring points 2a to 2i on the monitor 13a. First to ninth measuring point setting circuits 12a to 12i produce signals representing measuring points positioned by means of the switches SW01 to SW09 in synchronism with a pulse signal from the third frequency divider 7d of the signal generator 7. Switches SW2 to SW4, which are respectively coupled with the measuring point setting circuits 12a to 12c, selectively switch the output signals from the measuring point setting circuits 12a to 12c to a fifth adder 12 or to a 6th gate circuit 12g. Switches SW5 to SW7, which are respectively coupled with the setting circuits 12d to 12f, selectively switch the output signals from the measuring point setting circuits 12d to 12f to a 6th adder 12k or to a 7th gate circuit 12r of the measuring point select unit 12B. Switches SW8 to SW10, which are respectively coupled with the measuring point setting circuits 12g to 12i, selectively switch the output signals from the measuring point setting circuits 12g to 12i to a 7th adder 12l or to an 8th gate circuit 12s of the measuring point select unit 12B. The 5th adder 12j adds together the output signals from the measuring point setting circuits 12a to 12c. The 6th adder 12k adds together the output signals from the measuring point setting circuits 12d to 12f. The 7th adder 12l adds together the output signals from the measuring point setting circuits 12g to 12i. A 3rd gate circuit 12m produces the output signal (position signal) from the 5th adder 12j in synchronism with the output signal for scanning the first beam mark 3a from the first scanning control circuit 8a for the first beam mark 3a. A 4th gate circuit 12n produces an output signal (position signal) from the 6th adder 12k in synchronism with an output signal for scanning the second beam mark 3b from the second scanning control circuit 8b for the second beam mark 3b. A gate circuit 12n produces an output signal for scanning the second beam mark 3b from the second scanning control circuit for the second beam mark 3b. A 5th gate circuit 12P produces an output signal (position signal) for scanning the 3rd beam mark from the 7th adder 12l in synchronism with the output signal from the 3rd scanning control circuit 8c for the 3rd beam mark 3c. An 8th adder 12p adds the output signals from the gate circuits 12m, 12n and 12o. The output signal from the 8th adder 12p is applied as a signal for providing dots of the blood flow measuring points on the monitor screen, to the 3rd adder 10a of the display mode controller 10.

The measuring point select unit 12B is comprised of a 6th gate circuit 12q, a 7th gate circuit 12r, an 8th gate circuit 12s, a 9th adder 12t, and a modulation circuit 12p. The 6th gate circuit 12q produces output signals (position signals) from the setting circuits 12a to 12c in synchronism with an output signal (scanning signal) from the first scanning control circuit 8a. The 7th gate circuit 12r produces output signals (position signals) from the setting circuits 12d to 12f in synchronism with the output signal (scanning signal) from the scanning control circuit 8b. The 8th gate circuit 12s produces output signals (position signals) from the measuring point setting circuits 12g to 12i in synchronism with the output signal (scanning signal) from the 3rd scanning control circuit 8c. The 9th adder 12t sums the output signals from the gate circuits 12q, 12r and 12s. The fourth frequency divider 12u frequency-divides the pulse signal from the 3rd divider 7d into a pulse signal at frequency less than several Hz. A modulation circuit 12p modulates an output signal indicating a blood flow measuring point to be selected, which is derived from the 9th adder 12t by an output pulse signal from the 4th divider 12u into a signal changing between two potential levels.

The switches SW2 to SW10 operate interlocking with one another and the switch SW1 in the measuring point setting circuit 11. When the switch SW6 is switched to the contacts "b", as shown in FIG. 9, the remaining switches SW2 to SW5 and SW7 to SW10 are connected to the contacts "a". At this time, the switch SW1 is connected to the contact "b". When the switch SW2 is connected to the contact "b", the other switches SW3 to SW10 are connected to the contacts "a" and the switch SW1 is connected to the contact "a". When the switch SW10 is connected to the contact "b", the other switches SW2 to SW9 are connected to the contacts "a" and the switch SW1 is connected to the contact "c".

The operation of the ultrasonic pulse Doppler apparatus shown in FIG. 3A to FIG. 9 will be described.

The power source (not shown) is turned on to operate the signal generator 7. Then, the signal generator 7 produces necessary pulse signals for transmission to the scanning controller 8, the display mode controller 10 and the blood flow velocity measuring point setting circuit 11. An output signal from the first adder 8f of the scanning controller 8 is applied to the transducer controller 9 to drive the probe 14. The probe 14 driven projects an ultrasonic beam into an object under diagnosis in a sectorial scanning manner. The probe 14 converts the echo signals from the object into electrical signals. The electrical signal is amplified by the T/R circuit 9b is inputted to the 3rd adder 10a of the display mode controller 10. The display mode controller 10 receives signals indicating the measuring points 2a to 2i from the 8th adder 12p in the measuring point setting circuit 12, a B mode image signal containing the output signals representing positions of the beam marks 3a to 3c derived from the second adder 8g of the scanning controller 8, and the echo signal from the transducer controller 9. Upon receipt of these signals, the display mode controller 10 operates to dislay a B mode image, beam marks 3a to 3c, and blood flow velocity measuring points 2a to 2i on the monitor 13a.

A case where an M mode image and a blood flow velocity signal at a desired measuring point are displayed on the monitor 13b, will now be described. For selecting the blood flow velocity measuring point 2e on the beam mark 3b, the second beam mark 3b is horizontally moved by means of the switch SWM1 to set the same mark to a desired position on the monitor screen 13a, while visually observing the second beam mark 3b on the monitor screen 13a. Then, the switch SW6 is set to the contact "a". Under this condition, the switch SW05 is operated to vertically move the measuring point 2e selected along the beam mark 3b to a desired position.

Subsequently, the switch SW6 is switched to the contact "b". At this time, the switch SW1 is switched to the contact "b" interlocking with the operation of the switch SW6. And the other switches SW2 to SW5 and SW7 to SW10 are fixed at the contacts "a". As the result of switching of the contact "b" to the switch SW1, the second beam mark 3b is selected as a beam mark on which the measuring point 2e to be selected lies. Upon switching the switch SW6 to the contact "b", the position signal set by the measuring point setting circuit 12e is applied, as a signal indicating the selected blood flow measuring point, through the 7th gate circuit 12r and the 9th adder 12t to the Doppler signal detecting circuit 10b. In the Doppler signal detecting circuit 10b, the Doppler signal is extracted from the echo signal produced from the T/R circuit 9b by the signal indicating an output signal for indicating the selected measuring point derived from the 9th adder 12t. Further, the Doppler signal is produced in synchronism with the M mode image scanning signal from the first gate circuit 7e. The output Doppler signal is added to the M mode image signal from the 3rd adder 10a in the 4th adder 10d. The added signal is applied to the M mode image display control circuit 10e. The control circuit 10e is supplied with an output signal as an M mode rate pulse signal from the first gate circuit 7e. On the basis of these signals, the display control circuit 10e produces the M mode image scanning signal, the Doppler signal and the M mode image signal. These output signals from the display control circuit 10e is applied to the monitor 13b. Then, the monitor 13b displays the M mode and the blood flow velocity at the selected measuring point 2e.

The output signal for indicating the selected measuring point derived from the 9th adder 12t in the measuring point 12B is inputted to the modulation circuit 12v. In the modulation circuit 12v, it is modulated by the output pulse signal from the 4th frequency divider 12u into a voltage signal changing between two levels. The modulated signal is applied to the 8th adder 12p. The 8th adder 12p adds together the output signals from the 3rd to 5th gate circuits 12m, 12n and 12o. The signal representing the addition is applied to the 3rd adder 10a of the display mode controller 10a. As a result, on the monitor 13a, only the measuring point 2e flickers. Seeing the flickering of the measuring point, an observer knows that the blood flow velocity is measured at the measuring point 2e now flickering on the monitor 13b.

In switching the selected measuring point 2e to another measuring point 2a, for example, for displaying the blood flow velocity signal at the measuring point 2e on the monitor 13b, all the observer has to do is to switch the switch SW2 in the measuring point setting unit 12A to the contact "b". Through the circuit operation similar to that described relating to the measuring point 2e, the monitor 13a displays the blood flow velocity signal at the measuring point 2a on the monitor 13b and the M mode image at the beam mark 3a bearing the measuring point 2a are displayed, while the measuring point 2a flickers on the monitor 13a.

As described above, in the ultrasonic pulse Doppler apparatus, a tomogram at a part to be observed is displayed on one display screen. At the same time, a blood flow velocity is dislayed in a manner that a plurality of blood flow velocity measuring points are set on and along the beam marks, and one desired measuring point is selected from those measuring points by a simple switching operation, while observing the tomogram. Thus, since the selecting operation is simple, time taken from the select operation to the display of the blood flow signal on the other monitor is relatively short. No deterioration of the reliability of the blood flow velocity measurement arises from time delay. Further, the selected measuring point can be changed by one time switching operation, the blood flow velocities at a plurality of measuring points can be displayed at short time intervals. The flickering of the selected measuring point enables an observer to clearly know the correspondence of a blood flow velocity signal displayed on one monitor and the selected measuring point. Thus, the Doppler apparatus according to the present invention provides a highly reliable diagnosis data.

It should be understood that the present invention is not limited by the above-mentioned embodiment, but may variously be modified and changed. For example, the number of beam marks and the measuring points may be suitably selected. The filckering display of the selected measuring point may be substituted by any other suitable display such as an enlarged dot or a shape changing dot.

What is claimed is:

1. An ultrasonic pulse Doppler apparatus comprising:
    an ultrasonic probe for transmitting ultrasonic beam into an object and receiving the echoes from said object;
    a first processing means for processing the echoes received by said probe to form data of a B scan tomogram of said object;
    a first display means for displaying the B scan tomogram;
    beam mark setting means for setting at least one beam mark on the displayed B scan tomogram;
    measuring point presetting the positions of means for a plurality of blood flow measuring points on said beam mark;
    measuring point selecting means for selecting any one blood flow measuring point from said plurality of blood flow measuring points;
    a second processing means for processing the echoes received by said probe to form a signal of a blood flow velocity at a selected measuring point;
    a second display means for displaying the blood flow velocity at the selected measuring point; and
    modulating means for distinguishing the selected measuring point on said displayed beam mark from other measuring points on said beam mark.

2. An ultrasonic pulse Doppler apparatus comprising:
    an ultrasonic probe for transmitting ultrasonic beam into an object and receiving the echoes from said object;
    a first processing means for processing the echoes received by said probe to form data of a B mode tomogram of said object;
    a first display means for displaying the B scan tomogram;
    beam mark setting means for setting a plurality of beam marks on the displayed B scan tomogram;
    measuring point presetting the positions of a plurality of blood flow measuring points on each of said beam marks;
    beam mark selecting means for selecting any one of said plurality of beam marks;
    measuring point selecting means for selecting any one of said plurality of blood flow measuring points on the selected beam mark;
    a second processing means for processing the echoes received by said probe to form a signal of a blood flow velocity at the selected measuring point;
    a second display means for displaying the blood flow velocity at the selected measuring point; and
    modulating means for distinguishing said selected measuring point on the selected displayed beam mark from other measuring points.

3. An ultrasonic pulse Doppler apparatus according to claim 2, wherein said measuring point selecting means interlocks with said beam mark selecting means so that said measuring point selecting means operates to select a blood flow measuring point when said beam mark selecting means operates to select a beam mark on which the selected measuring point exists.

4. An ultrasonic pulse Doppler apparatus comprising:
an ultrasonic probe for transmitting an ultrasonic beam into an object and receiving the echoes from said object;
a first processing means for processing the echoes received by said probe to form data of a B scan tomogram of said object;
a first display means for displaying the B scan tomogram;
beam mark setting means for setting at least one beam mark on the B scan tomogram;
measuring point setting means for simultaneous setting a plurality of blood flow measuring points on said at least one beam mark, the location of each such point being independently adjustable of each other such point;
measuring point selecting means for selecting any one blood flow measuring point from said plurality of blood flow measuring points;
a second processing means for processing the echoes received by said probe to form a signal of a blood flow velocity at said selected blood flow measuring point;
a second display means for displaying the blood flow velocity at the selected measuring point; and
modulating means for distinguishing the selected measuring point on said beam mark from other measuring points on said beam mark.

5. An ultrasonic pulse Doppler apparatus comprising:
an ultrasonic probe for transmitting ultrasonic beam into an object and receiving the echoes from said object;
a first processing means for processing the echoes received by said probe to form data of a B mode tomogram of said object;
a first display means for displaying the B scan tomogram;
beam mark setting means for simultaneously setting a plurality of beam marks on the B scan tomogram;
measuring point setting means for simultaneously setting a plurality of blood flow measuring points on each of said beam marks, the location of points on each such beam mark being independently adjustable of the location of points on each other such beam mark;
beam mark selecting means for selecting any one of said pluralty of beam marks;
measuring point selecting means for selecting any one of said plurality of blood flow measuring points on the selected beam mark, said measuring point selecting means interlocking with said beam mark selecting means so that said measuring point selecting means operates to select a blood flow measuring point when said beam mark selecting means operates to select a beam mark on which the selected measuring point exists;
a second processing means for processing the echoes received by said probe to form a signal of a blood flow velocity at the selected measuring point;
a second display means for displaying the blood flow velocity at the selected measuring point; and
modulating means for distinguishing said selected measuring point on the selected beam mark from other measuring points.

6. An ultrasonic pulse Doppler apparatus comprising:
ultrasonic probe means for transmitting an ultrasonic beam into an object and for receiving echoes of said beam reflected from said object;
first processing means, responsive to said received echoes, for producing data of a B scan tomogram representing said object;
first display means for displaying said B scan tomogram;
measuring point preselecting means for preselecting a plurality of points on said displayed tomogram;
means for selecting one of said plurality of preselected points;
second processing means responsive to said selected point for processing said received echoes to form a signal of blood flow velocity occurring at the point in said object corresponding to the selected point on said displayed tomogram representing said object; and
second display means, responsive to said blood flow velocity signal, for displaying indicia of said blood flow velocity at the same time the said first display means displays said B-scan tomogram.

7. An apparatus as in claim 6 wherein said measuring point preselecting means comprises:
means for specifying at least one line on said displayed tomogram; and
means for specifying a plurality of points on said line.

8. An apparatus as in claim 6 wherein:
said measuring point preselecting means comprises:
means for specifying a plurality of lines on said displayed tomogram; and
means for specifying a plurality of points on each of said lines; and
said means for selecting one of said plurality of preselected points comprises:
means for selecting one of said plurality of lines; and
means for selecting one of said plurality of points on said selected line.

* * * * *